United States Patent [19]

Cochran et al.

[11] Patent Number: 5,072,127
[45] Date of Patent: Dec. 10, 1991

[54] ENGINEERED VIDEO INSPECTING LIGHTING ARRAY

[75] Inventors: Don W. Cochran, Mayfield Village; James R. Austin, Mentor-on-the-Lake, both of Ohio

[73] Assignee: Pressco, Inc., Solon, Ohio

[21] Appl. No.: 622,349

[22] Filed: Nov. 29, 1990

Related U.S. Application Data

[63] Continuation of Ser. No. 429,780, Oct. 31, 1989, abandoned, which is a continuation-in-part of Ser. No. 336,642, Apr. 7, 1989, abandoned, and a continuation of Ser. No. 107,265, Oct. 9, 1987, abandoned, and a continuation of Ser. No. 409,148, Sep. 9, 1989, abandoned.

[51] Int. Cl.$^5$ .............................................. G01N 21/88
[52] U.S. Cl. ................................ 250/572; 250/223 B; 356/240; 358/106
[58] Field of Search ................... 250/571, 572, 223 B; 356/240, 241; 358/106, 101

[56] References Cited

U.S. PATENT DOCUMENTS

| 3,222,524 | 12/1965 | Lee ........................................ 250/106 |
| 3,746,784 | 7/1973 | Van Oosterhout ................... 178/6.8 |
| 3,903,416 | 9/1975 | Fox ........................................ 250/360 |
| 4,002,823 | 1/1977 | Van Oosterhout ................. 358/106 |
| 4,165,277 | 8/1979 | Frewin ................................. 209/3.3 |
| 4,217,491 | 8/1980 | Dufford, Jr. et al. ........... 250/223 R |
| 4,256,957 | 3/1981 | Ford et al. ...................... 250/223 B |
| 4,271,408 | 6/1981 | Teshima et al. ..................... 340/702 |
| 4,293,219 | 10/1981 | Ducloux ............................... 356/240 |
| 4,305,658 | 12/1981 | Yoshida ................................. 356/23 |
| 4,318,808 | 3/1982 | Atkinson ............................... 209/533 |
| 4,343,021 | 8/1982 | Frame ................................... 358/213 |
| 4,344,146 | 8/1982 | Davis, Jr. et al. .................. 364/522 |
| 4,364,088 | 12/1982 | Kubota ................................. 358/106 |
| 4,367,405 | 1/1983 | Ford ..................................... 250/223 |
| 4,380,025 | 4/1983 | Deane ................................... 358/106 |
| 4,385,233 | 5/1983 | Lovalenti ............................. 250/223 |
| 4,385,318 | 5/1983 | Miller ................................... 358/106 |
| 4,414,566 | 11/1983 | Peyton et al. ....................... 358/101 |
| 4,427,880 | 1/1984 | Kanade et al. ..................... 250/222.1 |
| 4,439,788 | 3/1984 | Frame ................................... 358/213 |
| 4,442,455 | 4/1984 | Huignard et al. ................... 358/209 |
| 4,446,481 | 5/1984 | Edamatsu et al. ................... 358/106 |
| 4,486,776 | 12/1984 | Yoshida ............................... 358/106 |
| 4,491,868 | 1/1985 | Berridge, Jr. et al. ............. 358/139 |
| 4,509,076 | 4/1985 | Yoshida ............................... 358/106 |
| 4,530,036 | 7/1985 | Conti ..................................... 362/32 |
| 4,567,551 | 1/1986 | Choate ................................... 362/398 |
| 4,581,632 | 4/1986 | Davis et al. .......................... 358/106 |
| 4,586,080 | 4/1986 | Hoyt et al. ........................... 358/106 |
| 4,595,289 | 6/1986 | Feldman et al. ..................... 356/237 |
| 4,604,648 | 8/1986 | Kley ..................................... 358/101 |
| 4,606,635 | 6/1986 | Miyazawa et al. ................... 356/240 |
| 4,677,473 | 6/1987 | Okamoto ............................. 358/101 |
| 4,697,076 | 9/1987 | Yoshida ............................... 356/240 |
| 4,731,649 | 3/1988 | Chang et al. ........................ 358/106 |
| 4,758,084 | 7/1988 | Tokumi et al. ...................... 356/240 |
| 4,764,681 | 8/1988 | Michalski et al. ................... 250/563 |
| 4,811,251 | 3/1989 | Minato ................................. 364/552 |
| 4,843,231 | 6/1989 | Caloyannis et al. ............ 250/223 B |
| 4,860,096 | 8/1989 | Long et al. .......................... 358/101 |
| 4,865,447 | 9/1989 | Shay ..................................... 356/240 |
| 4,912,318 | 3/1990 | Kajiura et al. ................. 250/223 B |

FOREIGN PATENT DOCUMENTS 341806 2/1989 European Pat. Off. .
336563 3/1989 European Pat. Off. .

OTHER PUBLICATIONS

Strober Head for Zapata Industries, Inc., Crown Inspection System (date unknown).

(List continued on next page.)

Primary Examiner—Davis L. Willis
Assistant Examiner—Que T. Le
Attorney, Agent, or Firm—Fay, Sharpe, Beall, Fagan, Minnich & McKee

[57] ABSTRACT

An engineered video inspection lighting system includes a three-dimensional array of solid-state light emitting diodes focused to an inspection area. A single high-current, low-duration pulse is applied to selected elements of the array. Light thus generated is passed through a diffuser and to a specimen. Light reflected from the specimen is received by a lens of a video camera disposed in an interior of the three-dimensional array. Data thus obtained is used to determine acceptability of the specimen in accordance with preselected standards.

18 Claims, 4 Drawing Sheets

ENGINEERED VIDEO INSPECTING LIGHTING ARRAY

This is a continuation of copending application Ser. No. 07/429,780 filed on Oct. 31, 1989, now abandoned, which is a continuation-in-part of co-ending U.S. application Ser. No. 336,642 filed Apr. 7, 1989, now abandoned as a file-wrapper continuation of U.S. application Ser. No. 107,265 filed Oct. 9, 1987, abandoned and co-pending U.S. application Ser. No. 409,148 filed Sept. 19, 1989, now abandoned, the contents of all of which are incorporated herein by reference.

BACKGROUND OF THE INVENTION

This application pertains to the art of video inspection, and more particularly to inspection systems for a sequence of generally uniform articles. The invention is particularly applicable to inspections of containers or components thereof, and will be described with particular reference thereto. It will be appreciated, however, that the invention has broader applications, such as in any video inspection environment or machine vision system.

Machine vision systems have secured a significant presence in industry, both in the area of robotic assembly systems as well as inspection systems to aid in quality control. A typical vision system includes a lighting system to light a specimen, and a camera for sensing light reflected therefrom. In a typical system, a digitized image is formed from light, reflected from the specimen, received by the camera. This digitized image data is then made available for controlling a robot arm, identifying the specimen, or determining acceptability of the specimen in accordance to specified standards.

A problem arises when inspecting specimens having curved surfaces or interior compartments. Conventional lighting systems are ineffective for obtaining images given that varying angles provide for mirror imaging of the light source on the specimen or reflection of light away from the camera's lens. As a result, inspections of such articles are at best imperfect or at worst impossible with present systems.

The present invention contemplates a new and improved video inspection system which overcomes the above-referred problems, and others, and provides a video inspection system which allows for accurate inspection of specimens having varying contours and internal portions.

SUMMARY OF THE INVENTION

In accordance With the present invention, there is provided a video inspection lighting apparatus which includes a plurality of directional light generating elements. A means is provided for securing each electronic light generating element into a three-dimensional array having an interior portion and an exterior portion, with each light generating element being mounted on the interior portion and directed to an associated lighting area. An aperture portion is defined in one area of the mounting means. A video camera, secured in the exterior portion of the lighting array, has a lens extending therefrom, through the aperture portion, generally into the interior of the array. A means is provided for supplying a current pulse to at least a portion of the light generating elements of the array, whereby illumination of an associated specimen disposed in the lighting area is accomplished.

In accordance with a more limited aspect of the present invention, means is provided for receiving image data from the video camera, and causing a comparison of the image data to data representative of an acceptable specimen.

In accordance with a yet more limited aspect of the present invention, means is provided for communicating image data obtained from the video camera to first and second signal processors. The first signal processor has a first selected gain level and the second signal processor has a second signal gain level different from that of the first data processor. Data obtained from the first and second signal processors is then independently compared to data representative of acceptability of a specimen under data obtained at the particular gain level.

An advantage of the present invention is the provision of a system which allows for engineered illumination, and video inspection, of items having varying contours.

Another advantage of the present invention is provision of a system which allows for isolation of selected portions of a specimen under consideration in accordance with lighting levels across that portion.

Yet another advantage of the present invention is a provision of a system which allows for simultaneous comparison of images at various intensity levels obtained from various portions of a single specimen to independently determine acceptability thereof in accordance with preselected standards.

Further advantages will become apparent to one of ordinary skill in the art upon a reading and understanding of the subject specification.

BRIEF DESCRIPTION OF THE DRAWINGS

The invention may take physical form in certain parts and arrangements of parts, preferred embodiments of which will be described in detail in this specification, and illustrated in the accompanying drawings which form a part hereof and wherein:

FIG. 3 illustrates a cross-sectional view of another embodiment of a lighting apparatus adapted for illumination of rib surfaced specimens, or the like.

DETAILED DESCRIPTION OF THE PREFERRED EMBODIMENTS

Figure 1:
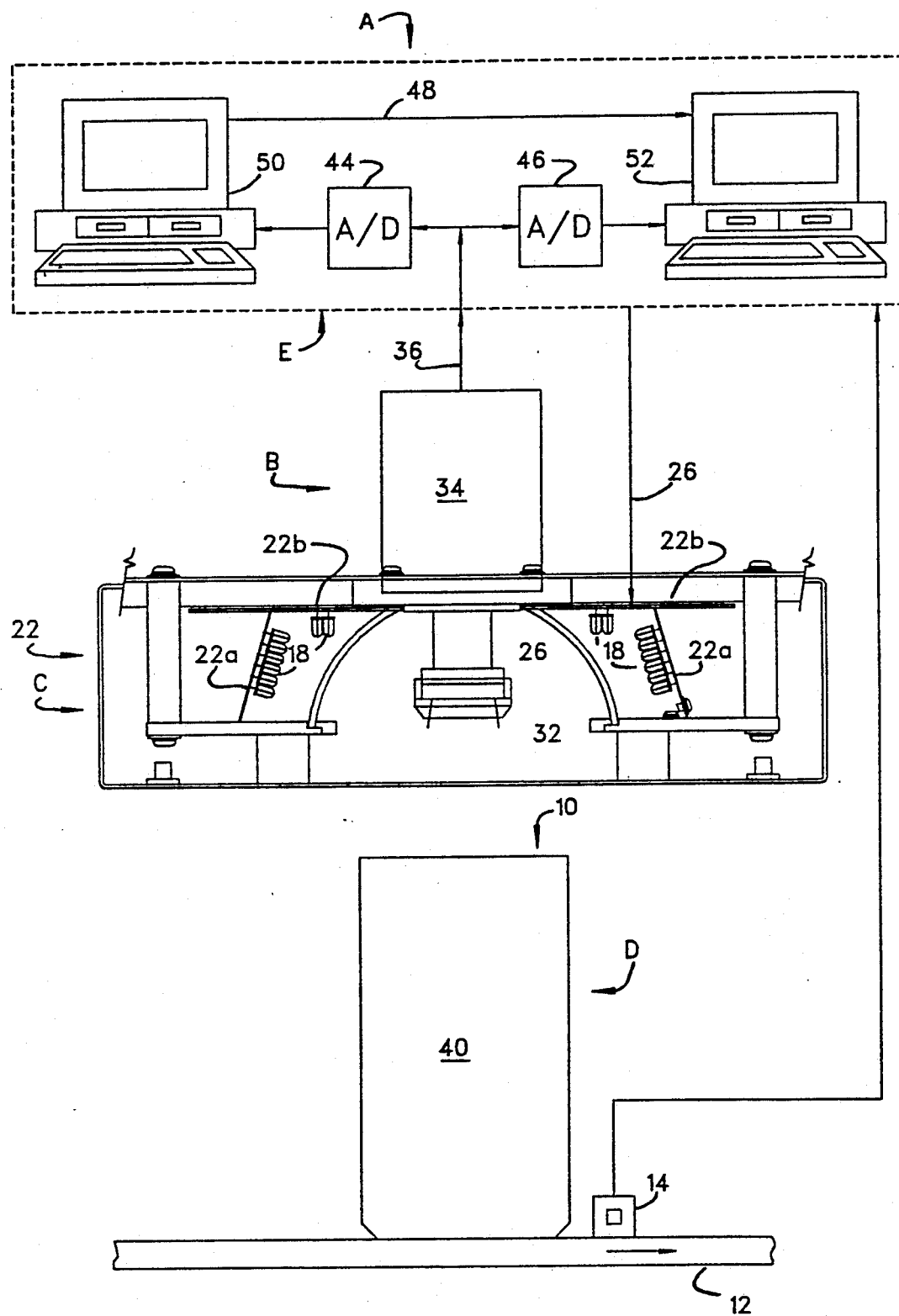
FIG. 1 illustrates a cross-sectional view of a system for illuminating, acquiring data, and analyzing acquired data, for video inspection of a specimen.

Turning now to the figures, Wherein the illustrations are for the purposes of describing of the preferred embodiments only, and not for the purpose of limiting the same, FIG. 1 illustrates a video inspection system A which includes a camera module B, a lighting unit C, a specimen D, and a data processing system E.

In the preferred embodiment, the specimen D is brought to an illumination area 10 by a conveyor belt or means 12. Presence of the specimen D within the illumination area 10 is suitably determined by a position sensor 14, illustrated as a photo sensitive detector, or other suitable tracking mechanism. In FIG. 1, the specimen D is illustrated as a beverage container 16, for which structure the illustrated system is particularly advantageous.

The lighting unit C includes a plurality of directional electronic light generating elements 18 which are, in the preferred embodiment, solid-state lighting emitting diodes, or the like. The elements 18 together form an array 22. The light generating elements 18 are secured on and directed into an interior portion of the array 20, by a circuit board or mounting means 22. The mounting means 22 forms a three-dimensional lighting array having an angled vertical portion 22a and a generally perpendicular portion 22b, both orientations being defined in relation to a single longitudinal axis or optical centerline of the camera module B. Particular constructions of the array 20 will be more easily visualized in conjunction with FIG. 4, described in more detail below.

Engineered lighting of specimens may be generally accomplished by regulating a time duration during which any or all elements are activated; regulating a magnitude of current supplied to any or all elements; or selectively enabling any or all of light emitting elements of the array. These factors provide means by which lighting conditions may be regulated or tuned to various specimens. In the preferred embodiment, bank switching of light emitting diodes is employed. That is to say, selected individual banks of light emitting elements are enabled during a specified illumination period. This is accomplished by software control of the data processing system E, as preselected by a human applicator, or alternatively, by automated feedback tuning in accordance with a suitable feedback algorithm.

Presence of a specimen D in viewing area 10, as sensed by position sensor 14, is communicated to the data processing system E. This, in turn causes a single short-duration, high-current pulse to be applied to selected of the elements 18 through path illustrated at 26. Light thus generated from enabled elements 18 is then preferably passed through an arcuate diffuser plate or means 26, which diffuser has an aperture portion 28 therethrough. Light, rendered more uniform by a passage thereof through the diffuser 26, is then exposed to specimen D disposed in the illumination area 10. Light reflected from the specimen D is then received by a lens portion 32, and there after applied to light sensitive elements disposed within a video camera means 34 of camera module B.

Although the illustration of camera module B evidences one camera therein, it will be appreciated that multiple camera means, sensitive along the same optical centerline, may be utilized. This may be accomplished by use of a beam-splitter arrangement disposed between the camera module B, and the specimen D. Such dual camera arrangements allow for independent analysis of various subportions of a specimen, or allow for alignment of an image in a feedback process.

In the illustrated embodiment, the lens portion 32 extends into the interior of the three-dimensional array 20, as well as into the interior of the arcuate diffuser 26. The lens portion 32 preferably includes a wide angle or "fisheye" lens having a high depth of field. This arrangement provides for maximizing the amount of light transmitted to a specimen, optimizing the angles at which the light travels to the specimen, and improving the integrity of a captured image.

As will be appreciated by one or ordinary skill in the art, the light thus exposed to the video camera means creates image data representative of the illuminated object. Image data is communicated from the video camera means 34, via connection 36, to the data processing system E.

Image data passed via connection 35 in the above-described manner includes data representative of all salient internal portions of the specimen D. It is to be realized, however, that present technology renders it difficult to immediately extract data representative of acceptability of an image given that various lighting subportions of the specimen D have been subjected to varying intensity levels, thus creating a wide swing in intensities over the entire specimen. In particular, for example, it will be appreciated that a rim portion 40 will be subject to an overall increase in intensity, over that of, for example, a bottom segment 42 of the specimen D. The present invention advantageously provides a system for allowing complete analysis of any such subportion, notwithstanding the wide swing in intensities over the specimen.

To accomplish this, the image data received from connection 36, which in the preferred embodiment is in analog form, is passed to first and second signal processing elements or means 44 and 46 respectively, each of which preferably includes an analog-to-digital ("A/D") convertor. Accordingly, image data received along a single optical centerline, from at least one camera, is conveyed to both signal process elements 44, 46.

The first and second A/D convertors of first and second signal processors 44 and 46 each have unique gain characteristics defined thereby, whereby various segments of the image data may be seized upon for analysis. A feedforward line 48 is also advantageously provided for communicating data from data processing element 50 to data processing element 52. Such data may include alignment data to fix a location for analysis by processing element 52.

In the preferred embodiment, outputs from first and second A/D convertors are communicated to first and second data processing elements 50 and 52, respectively. The use of two such data processing elements provides for high-speed, parallel image analysis. Each processing element 50 and 52 provides for a comparison of acquired, now digitized, image data to data representative of acceptable or unacceptable specimens. In the event that it is determined in either data processing element that the specimen is unacceptable, this data is made available to the system for rejection of the specimen at a point downstream on the conveyor means 12 from the illumination area 10.

Figure 2:
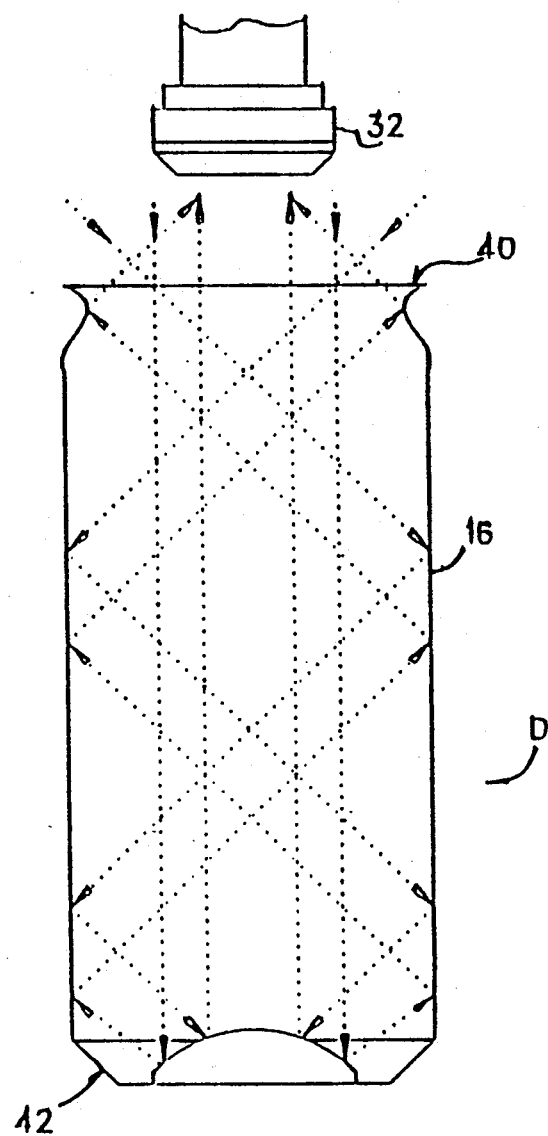
FIG. 2 illustrates, in detail, a lighting of a specimen in conjunction with the system of FIG. 1.

Turning now to FIG. 2, illumination of the specimen D illustrated as beverage container 16, by virtue of the lighting unit C of FIG. 1 will be understood more clearly. It will be seen from the figure that light entering the specimen D, is provided to all portions of the specimen. Lighting is obtained both directly, from the light generating elements 18 (FIG. 1), and indirectly from the lighting generating elements 18 via internal reflection from the walls, sides, and bottom of the specimen. It will be appreciated from a review of the figure that a significant portion of the light is reflected from various portions of the specimen to the lens portion 32, such as described in more detail above. The system therefore provides means for acquiring data of the entire specimen internally, sufficient to render determination of acceptability therefrom.

Figure 3:
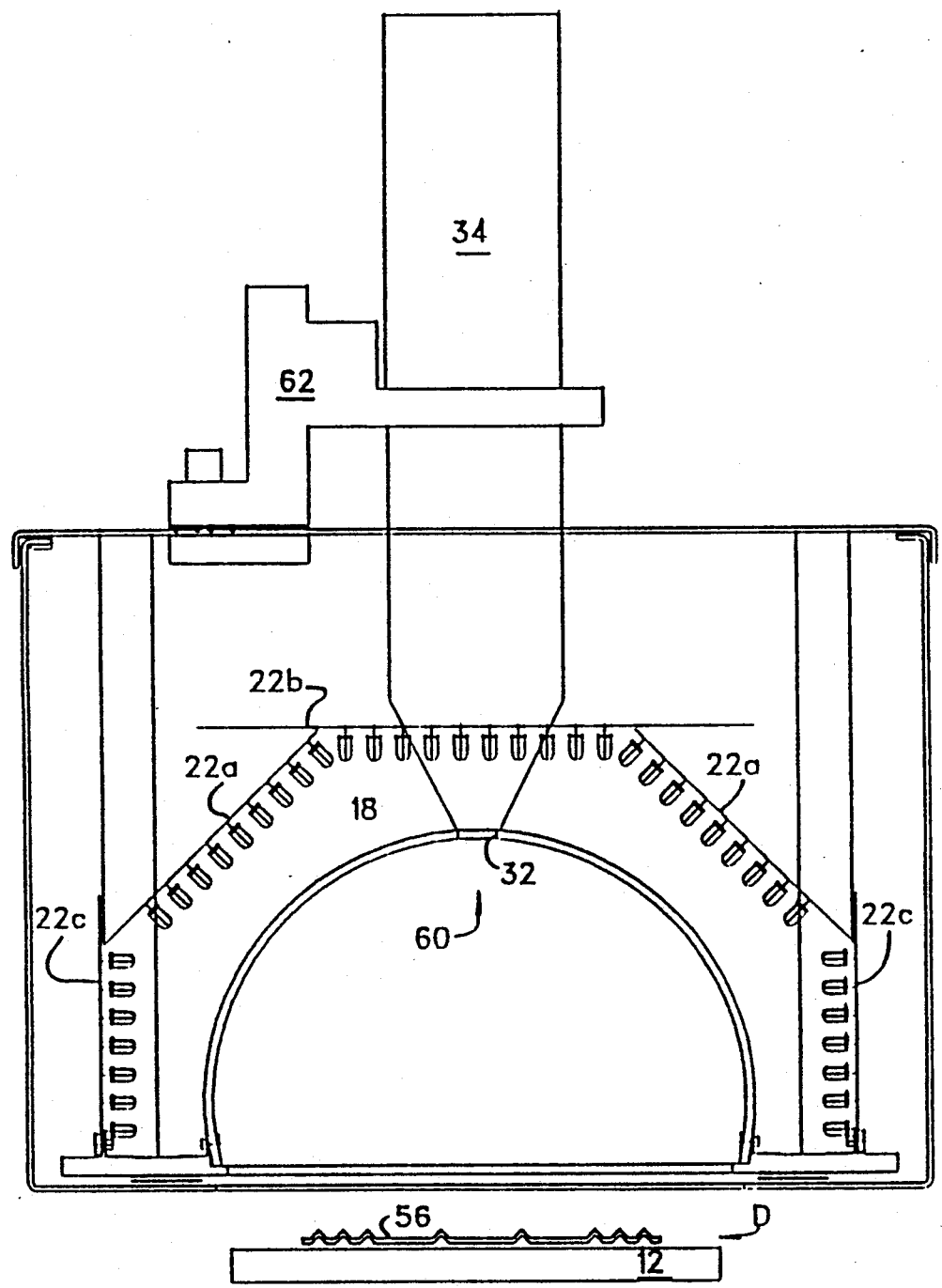

Turning now to FIG. 3, an embodiment of the subject invention specifically well suited for inspection of specimens which while generally planar, have ribbed or curved extension thereon will be described. Where possible, numeric indications have been carried forward from FIG. 1 to analogous structural components of FIG. 3.

In the embodiment of FIG. 3, the lighting unit C includes an array of directional lighting generating elements 18, again preferably comprised of solid-state LEDs. The mounting means 22 includes, in addition to portions analogous to that 22a and 22b of FIG. 1, portions 22c which are disposed in an orientation generally parallel to a longitudinal axis of video camera means 34. The construction of the lighting array of FIG. 3 provides for an additional number of angles at which light from individual elements 18 may be reflected from the specimen D, illustrated as a food can end 56, to lens portion 32 of video camera 34. As with the embodiment of FIG. 1, a arcuate diffuser means 26 is advantageously provided between the specimen D and the array of lighting emitting elements 18 to provide more even bathing of the specimen.

In the embodiment of FIG. 3, unlike that of FIG. 1, the lens portion 32 extends only to the arcuate diffuser 26, and not within an interior defined thereby. An opening 60 defined by diffuser 26 is advantageously kept at a minimum size to minimize reflections on the specimen, and to maximize available lighting to be applied from the array. This is suitably accomplished by utilization of a pinhole lens arrangement. The camera 34 is secured in this position via mounting bracket 62. As illustrated in the figure, a conical lens arrangement is suitably utilized to accomplish the desired minimization of the size of opening 60.

It will be appreciated that the structure of FIG. 3, although not illustrated, is advantageously applied to an environment, such as that of FIG. 1, including the data processing system E, conveyor means 12, and position sensor 14.

Figure 4:
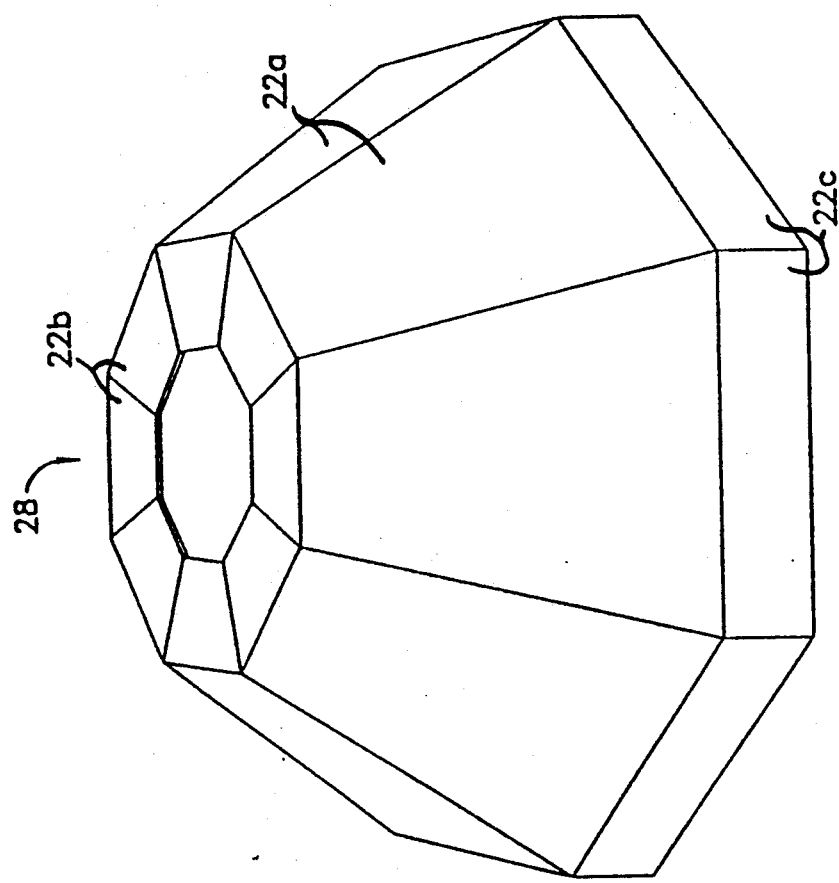
FIG. 4 illustrates a perspective view of a suitable construction three-dimensional lighting array as used in the apparatuses of FIGS. 1 and 3.

Turning now to FIG. 4, a perspective view of a suitable fabrication structure for mounting means 22 is presented. The perspective view affords ease in visualization not possible by the cut-away views of FIGS. 1 and 3. From the illustration, it will be seen that the mounting means is suitably fabricated from a series of trapezoidal-shaped portions or rectangular-shaped portions, interconnected as illustrated. The trapezoidal-shape portions are advantageously fabricated from printed-circuit board on which the directional lighting generating elements 18 are directly mounted. It will be appreciated that, in addition to the fabrication technic illustrated by FIG. 4, other techniques, such as utilization of flexible circuit board material are also suitably provided. Such circuit board provides an ability to have specialized, shaped or rolled, lighting arrangements to be adapted for use with a given structure.

The invention has been described with reference to a preferred embodiment. Obviously, modifications and alterations will occur to others upon a reading and understanding of this specification. It is intended to include all such modifications and alterations insofar as they come within the scope of the appended claims or the equivalents thereof.

What is claimed is:

1. An engineered lighting video inspection apparatus comprising:

a plurality of directional light generating elements;

mounting means for securing each light generating element of the plurality into a three-dimensional lighting array, the mounting means defining an interior portion and an exterior portion, wherein each of the light generating elements is secured to the interior portion such that it is directed to an associated lighting area;

the mounting means defining an aperture portion;

video camera means for generating image data from light exposed the lens extending therefrom; and means for securing the lens in the interior portion of the three-dimensional lighting array such that it extends through the aperture portion; and means for concurrently supplying a current pulse of a selected value to each of selected light generating elements of the array to provide illumination to the associated lighting area for illumination of an associated specimen.

2. The engineered lighting video inspection apparatus of claim 1 further comprising:

data processor means for receiving image from the video camera means resultant from illumination of the associated lighting area by application of the single current pulse to the portion of light generating elements of the array;

the data processor means including comparison means for comparing the image data to data representative of a range of acceptable image data; and means for determining acceptability of the associated specimen in accordance with an output of the comparison means.

3. The engineered video inspection system of claim 2 further comprising means for selectively altering light generating elements forming the selected light generating elements of the array to which the current pulse is applied.

4. The engineered lighting video inspection system of claim 2 further comprising;

arcuate diffuser means for selectively homogenizing light transmitted to the associated lighting area from the light generating elements, the diffuser means defining a second aperture portion; and means for securing the diffuser means between the three-dimensional lighting array and the associated lighting area such that the lens extends at least to the second aperture portion.

5. The engineered lighting video inspection apparatus of claim 4 wherein the image data generated by the video camera means includes analog data representative of an intensity value of each pixel of two dimensional array thereof, and wherein the apparatus further comprises:

the data processor means including a first signal processor having a first selected signal gain level, and a second signal processor having a second selected signal gain level different from the first selected signal gain level;

means for communicating the image data to the first signal processor whereby first processed image data is formed therefrom;

means for communicating the image data to the second signal processor whereby second processed image data is formed therefrom;

the comparison means including first correlation means for correlating the first processed image data to data representative of a range of acceptable image data of a first portion of the associated specimen; and the comparison means including second correlation means for correlating the second processed image data to data representative of acceptable image data of a second portion of the associated specimen uniquely defined from the first portion thereof.

6. The engineered lighting video inspection apparatus of claim 5 wherein the first and second comparing means include first and second processor elements, respectively, and wherein the data processor means further includes means for simultaneously enabling the first and second processor elements.

7. The engineered lighting video inspection system of claim 6 wherein the first signal processor includes a first analog-to-digital convertor and wherein the second signal processor includes a second analog-to-digital convertor, whereby the first and second processed signals include first and second digitized signals, respectively.

8. An engineered lighting video inspection apparatus comprising:
   lighting means for supplying a single high intensity, short duration light pulse to an associated specimen;
   video camera means, including a lens portion, for generating image data from received light of the light pulse into the lens portion after reflection thereof off the associated specimen;
   first and second signal processor means having uniquely defined first and second gain levels, respectively;
   means for communicating at least a portion of the image data to the first and second signal processors, whereby first and second processed signals are formed therefrom, respectively, from received image data;
   first and second data processing means for comparing received signal data with data representative of acceptable specimens to determine acceptability thereof; and
   means for communicating the first and second processed signals to the first and second data processors, respectively.

9. The engineered lighting video inspection apparatus of claim 8 further comprising means for simultaneously performing comparisons with the first and second data processors.

10. The engineered lighting video inspection apparatus of claim 9 wherein the video camera means includes means for generating the image data as data representative of a two dimensional array of pixels, each pixel having gray-scale level representative of an intensity of reflected light associated therewith.

11. The engineered lighting video inspection apparatus of claim 10 wherein:
   the first and second signal processor means each include an analog-to-digital convertor, whereby the first and second processed signals each include a digitized representation of an image of the associated specimen;
   the first and second data processors each include means for comparing each of the first processed signals with digitized data representative of acceptable specimens.

12. The engineered lighting video inspection apparatus of claim 11 wherein the lighting means includes:
   a plurality of directional electronic light generating element;
   mounting means for securing each element of the plurality into a three-dimensional lighting array, the mounting means defining an interior portion and an exterior portion, wherein each of the light generating elements is secured to the interior portion such that is generally directed to the associated specimen;
   the mounting means defining an aperture portion.

13. The engineered lighting video inspection apparatus of claim 12 further comprising means for securing the lens such that it extends generally to the aperture portion from the exterior portion.

14. The engineered lighting video inspection apparatus of claim 12 further comprising means for securing the lens such that it extends through the aperture portion into the interior portion defined by the mounting means.

15. An engineered lighting video inspection apparatus comprising:
   a lighting array including,
      a plurality of directed light generating elements;
      mounting means for securing each element of the plurality into a three-dimensional lighting array, the mounting means defining an interior portion and an exterior portion, wherein each of the lighting elements is secured to the interior portion such that it is directed to an associated lighting area, and
      the mounting means defining an aperture portion;
   video camera means including a lens portion;
   means for securing the video camera means in relation to the lighting array such that the lens portion extends through the aperture portion, terminating in the interior portion;
   means for conveying a series of associated specimens to the associated lighting area;
   means for determining a presence of each of the series of associated specimens within the lighting area;
   means for selectively supplying current to the plurality of lighting elements, whereby an associated specimen is illuminated by light resultant therefrom;
   means for communicating image data generated by the video camera means from light reflected from an illuminated associated specimen into the lens portion thereof;
   means for communicating the image data to first and second analog-to-digital conversion means, each having uniquely defined gain levels, whereby first and second digitized image data portions are formed;
   first comparing means for comparing the first digitized image data portion to data representative of acceptability of a specimen corresponding to digitized data processed at a first gain level;
   second comparing means for comparing the second digitized image data portion to data representative of acceptability of a specimen corresponding to digitized data processed at a second gain level.

16. The engineered lighting video inspection system of claim 15 wherein each of the first and second comparing means included independent data processors.

17. The engineered lighting video inspection system of claim 16 further comprising means for determining acceptability of each of the series of associated specimens in accordance with an output of at least one of the first and second comparing means.

18. The engineered video inspection system of claim 2 further comprising means for selectively altering light generating elements forming the selected light generating elements of the array to which the current pulse is applied.

* * * * *